US012766291B1

(12) United States Patent
Taylor, Jr. et al.

(10) Patent No.: US 12,766,291 B1
(45) Date of Patent: Oct. 20, 2026

(54) SYSTEMS AND METHODS FOR A FEMALE EXTERNAL CATHETER

(71) Applicants: Myron Eugene Taylor, Jr., Brookeville, MD (US); Robert L Hester, Derwood, MD (US)

(72) Inventors: Myron Eugene Taylor, Jr., Brookeville, MD (US); Robert L Hester, Derwood, MD (US)

( * ) Notice: Subject to any disclaimer, the term of this patent is extended or adjusted under 35 U.S.C. 154(b) by 0 days.

(21) Appl. No.: 19/374,723

(22) Filed: Oct. 30, 2025

(51) Int. Cl.
*A61M 25/00* (2006.01)
*A61M 25/01* (2006.01)

(52) U.S. Cl.
CPC ...... *A61M 25/005* (2013.01); *A61M 25/0054* (2013.01); *A61M 25/0105* (2013.01); *A61M 2025/0166* (2013.01); *A61M 2210/1078* (2013.01)

(58) Field of Classification Search
CPC .. A61M 2210/1078; A61M 2202/0496; A61M 2202/0498; A61M 27/008; A61M 27/00; A61M 2025/0063; A61M 25/005; A61M 25/0138
See application file for complete search history.

(56) References Cited

U.S. PATENT DOCUMENTS 5,523,092 A * 6/1996 Hanson ..................... A61F 2/06 604/523
5,762,630 A * 6/1998 Bley ....................... A61L 29/14 604/524
6,264,611 B1 * 7/2001 Ishikawa ............. A61B 5/6848 600/488
6,358,229 B1 * 3/2002 Tihon ................ A61M 25/0017 604/164.01
2010/0152663 A1 * 6/2010 Darr .................. A61M 25/0152 604/164.01
2013/0158675 A1 * 6/2013 Hutchins, III .... A61M 25/0041 623/23.66
2018/0200480 A1 * 7/2018 Chiu ................. A61M 25/0097
2021/0228795 A1 * 7/2021 Hughett .................. A61F 5/451

* cited by examiner

*Primary Examiner* — Nilay J Shah
(74) *Attorney, Agent, or Firm* — QuickPatents; Kevin Prince

(57) ABSTRACT

Systems and techniques may generally be used for external urinary collection using a formable female external catheter system. The system may include an elongated, flexible catheter body comprising catheter tubing and a semi-rigid, malleable internal stent disposed longitudinally within the catheter body. The internal stent may be deformable and may have sufficient column strength to resist radial collapse of the catheter body under negative pressure. The internal stent may extend through the catheter to provide structural support, and its deformability may allow the catheter body to be selectively reconfigured to conform to a specific patient anatomy while maintaining a shaped configuration during use. In some aspects, the catheter body may include a compliant outer shell and a fluid-wicking inner layer, the stent may include a distal ancillary extension, and terminal docking features may receive functional modules such as biosensor pods or dispenser pods to monitor physiological parameters or dispense substances.

18 Claims, 9 Drawing Sheets

SYSTEMS AND METHODS FOR A FEMALE EXTERNAL CATHETER

CROSS REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

The present disclosure generally relates to external urinary collection and noninvasive urinary management devices and more particularly to female external catheters and patient-interface systems for vacuum-assisted urine collection.

BACKGROUND

In the field of external urinary collection for female patients, conventional devices generally rely on fixed geometries, adhesive interfaces, and flexible bodies connected to suction sources. Clinical use environments may involve variable patient anatomies, changes in body habitus, repositioning, and different negative pressure levels. Prior systems may experience poor conformity to anatomical surfaces, leading to leakage, skin exposure to moisture, and the need for frequent repositioning. Flexible catheter walls may deform inward under suction, which may reduce lumen openness and intermittently occlude flow. In devices incorporating chambers upstream of drainage tubes, negative pressure may draw a chamber bottom toward a tube entrance, further restricting throughput. Limitations in adjustability, comfort, and workflow efficiency may be observed, and integration with bedside monitoring or targeted local delivery may be limited without adding separate equipment and lines.

Therefore, there is a need for a device that maintains patency under clinically relevant negative pressure levels, conforms to variable anatomical contours without excessive reliance on adhesives or high wall stiffness, reduces leakage and pooling at the skin interface, mitigates occlusion modes including chamber-bottom draw-in at a tube inlet, accommodates postural changes and repositioning, offers scalable sizes and material options suitable for diverse patient populations, and optionally supports bedside monitoring and/or localized delivery without adding invasive hardware.

SUMMARY OF THE INVENTION

Embodiments of the invention may include one or more of the following features. These features may be used singly, or in combination with each other.

The present device maintains patency under clinically relevant negative pressure levels, conforms to variable anatomical contours without excessive reliance on adhesives or high wall stiffness, reduces leakage and pooling at the skin interface, mitigates occlusion modes including chamber-bottom draw-in at a tube inlet, accommodates postural changes and repositioning, offers scalable sizes and material options suitable for diverse patient populations, and optionally supports bedside monitoring and/or localized delivery without adding invasive hardware.

In some aspects, the device may include an elongated, flexible catheter body comprising catheter tubing and a semi-rigid, malleable internal stent disposed longitudinally within the body. The internal stent may extend through the catheter to provide structural support, may be deformable to allow selective reconfiguration to a patient-specific arcuate profile, and may possess sufficient column strength to resist radial collapse when subjected to a negative pressure differential. The catheter body may include a multi-laminate construction with a compliant outer shell and a fluid-wicking inner layer having a textured, fibrous microstructure to transport liquid away from the interface. A proximal region may be coupled to a connector suitable for fluid communication with a vacuum source, and internal geometries may be arranged to maintain an open flow path.

In various embodiments, terminal docking features on the internal stent may receive functional modules such as biosensor pods and dispenser pods. A biosensor pod may monitor physiological parameters including pH, temperature, acidity, or presence of blood. A dispenser pod may deliver a medication or a dye via controlled outlets toward a wicking pathway. A distal portion of the internal stent may include an ancillary support extension to reinforce a distal region against inward wall movement. The device may be manufactured by inserting the malleable stent into a longitudinal bore and plastically deforming the stent to impart a persistent, non-linear configuration.

The above advantages and features are of representative embodiments only and are presented only to assist in understanding the invention. It should be understood that they are not to be considered limitations on the invention as defined by the claims. Additional features and advantages of embodiments of the invention will become apparent in the following description, from the drawings, and from the claims.

Aspects described below also include Systems and Methods for a Female External Catheter.

BRIEF DESCRIPTION OF THE DRAWINGS

The appended figures depict certain features of the various aspects described herein and are not to be considered limiting of the scope of this disclosure.

DETAILED DESCRIPTION OF THE PREFERRED EMBODIMENT

Figure 1:
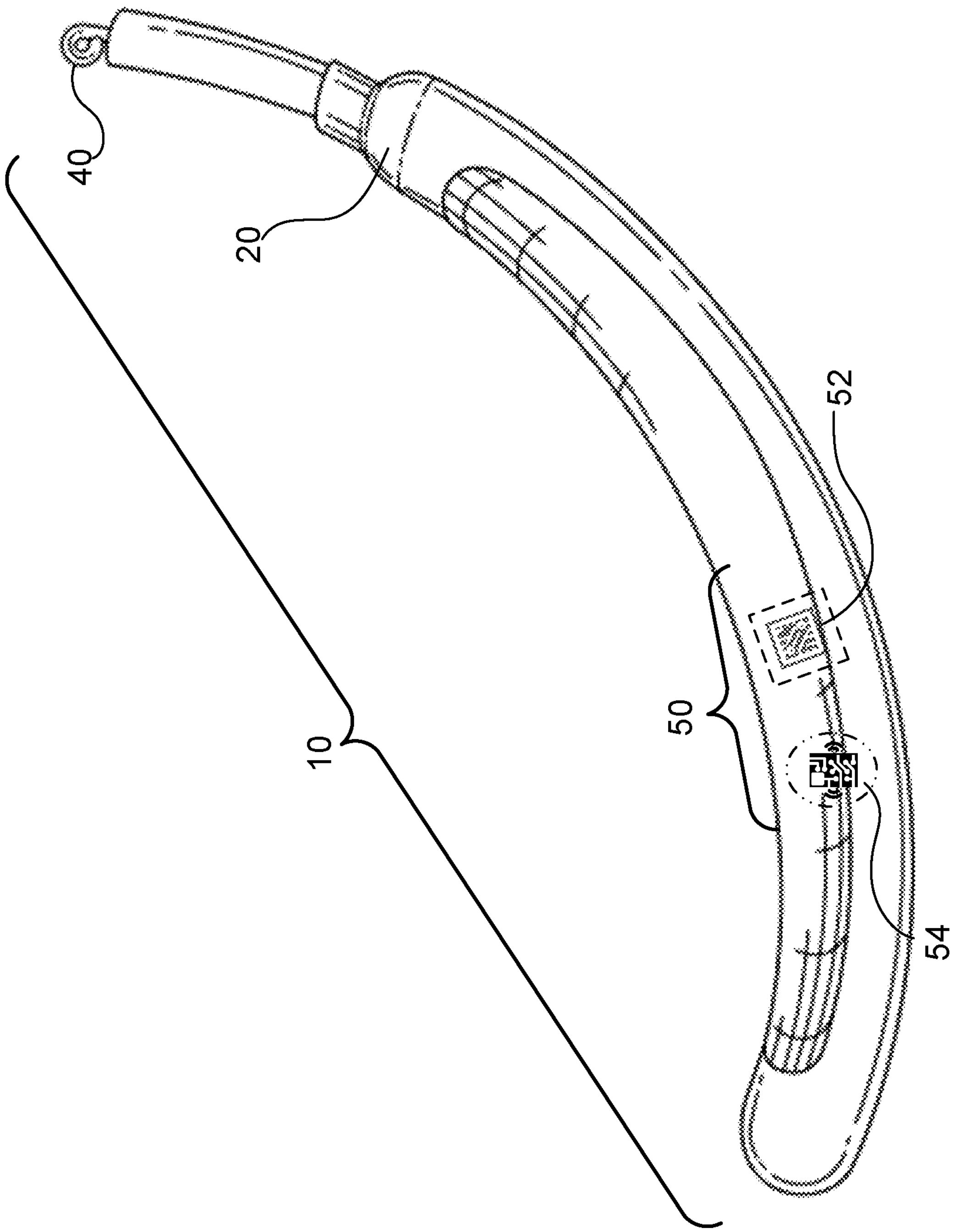
FIG. 1 illustrates a perspective view of a formable external catheter system with malleable internal stent.

In the following detailed description, numerous specific details are set forth by way of examples to provide a thorough understanding of the relevant teachings. However, it should be apparent that the present teachings may be practiced without such details. In other instances, well-known structures, functions, methods, procedures, components, and/or circuitry have been described at a relatively high level, without detail, to avoid unnecessarily obscuring aspects of the present teachings.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements but can also mean a singular element.

As noted, existing limitations in adjustability, comfort, and workflow efficiency may be observed, and integration with bedside monitoring or targeted local delivery may be limited without adding separate equipment and lines. To address the challenges associated with traditional methods of catheterization, techniques are described that implement SYSTEMS AND METHODS FOR A FEMALE EXTERNAL CATHETER.

The illustrative embodiments are described with respect to certain types of machines. The illustrative embodiments are also described with respect to other scenes, subjects, measurements, devices, data processing systems, environments, components, and applications only as examples. Any specific manifestations of these and other similar artifacts are not intended to be limiting to the disclosure. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the disclosure, either locally at a data processing system or over a data network, within the scope of the disclosure. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific surveys, code, hardware, algorithms, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable devices, structures, systems, applications, or architectures therefor, may be used in conjunction with such embodiment of the disclosure within the scope of the disclosure. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Referring to FIG. 1, which illustrates a perspective view of a formable external catheter system 10, the formable external catheter system 10 may include an elongated, flexible catheter body 20 and a semi-rigid, malleable internal stent 40 that may be disposed longitudinally within the catheter body 20. In some aspects, the catheter body 20 may present an arcuate profile that may be contoured to conform to an anatomical surface, and the malleable internal stent 40 may extend through the catheter body 20 to provide structural support that may resist radial collapse during use. In certain aspects, the catheter body 20 may be shaped as a crescent-like elongate member that may include catheter tubing and a distal region that may establish a non-invasive interface with a patient while fluid is drawn toward a proximal connection, for example. In many aspects, the malleable internal stent 40 may be selectively deformable by hand to reconfigure the arcuate profile of the catheter body 20 and may maintain a shaped configuration during typical handling, placement, or negative pressure operation.

In some aspects, the catheter body 20 may include materials and geometries that may balance compliance and structural stability. The catheter body 20 may include a compliant outer wall that may be formed of a medical-grade silicone elastomer, a polyurethane elastomer, a thermoplastic elastomer, a latex-free elastomer, and/or a multilaminate composite that may include a fluid-wicking inner layer. In various aspects, the fluid-wicking inner layer may include a textured, fibrous microstructure that may be configured to transport liquid via capillary action away from an interface region, and the outer wall may present a smooth surface to attenuate localized pressure. In certain aspects, an inner concave surface of the catheter body 20 may include a plurality of transverse markings that may be configured to enhance flexibility in controlled bend zones and to cooperate with deformation by the malleable internal stent 40 to achieve a persistent, non-linear configuration, for instance. In other aspects, wall thickness, durometer, and local reinforcement of the catheter body 20 may be tailored so the catheter body 20 may maintain lumen patency across a range of negative pressure differentials that may be used during clinical suction.

In many aspects, the malleable internal stent 40 may include a wire-like support that may exhibit sufficient column strength to resist radial collapse of the catheter body 20 when a negative pressure source is applied through catheter tubing. The malleable internal stent 40 may include a plastically deformable segment that may be reconfigured to a target curvature and may remain shape-retentive during use while still permitting incremental adjustments. In some implementations, the malleable internal stent 40 may be fabricated from a memory metal alloy such as nitinol, a malleable stainless steel, an aluminum-bronze alloy, a spring-tempered polymer-composite rod, and/or a hybrid metal-polymer laminate that may be tuned for flexural modulus and column strength. In certain aspects, a distal end of the malleable internal stent 40 may include an ancillary support structure comprising an extension that may provide structural reinforcement to a distal end region of the catheter body 20 to mitigate inward wall deflection under suction. In other aspects, terminal docking features of the malleable internal stent 40 may be integrally formed coiled end-loops, hooks, saddles, or sockets that may be configured to mechanically receive a module without tools.

In some aspects, at least one functional module 50 may be mechanically coupled to the malleable internal stent 40. The functional module 50 may be removable, interchangeable, and/or permanently affixed, and the coupling may be by friction fit, captured loop, snap fit, bayonet twist, or an interference sleeve that may seat against a terminal docking feature of the malleable internal stent 40. In certain aspects, a biosensor pod 52 may be positioned at ends of the malleable internal stent 40 and may include a sensor configured to monitor at least one physiological parameter selected from pH, temperature, acidity, and presence of blood. In various aspects, the biosensor pod 52 may include a microelectronic sensing element, leads, and an encapsulation that may be biocompatible, and the biosensor pod 52 may locally sample liquid or vapor proximate to the catheter body 20 and may communicate data by wired or wireless means, for instance. In other aspects, a dispenser pod 54 may be configured to dispense a substance proximate to the interface region of the catheter body 20, and the substance may include a medication or a dye, where a metering or wicking outlet may be oriented to deliver toward a wick or shell surface of the catheter body 20.

In various aspects, the formable external catheter system 10 may be assembled so that the malleable internal stent 40 extends substantially along a length of the catheter body 20, with the catheter body 20 establishing a longitudinal bore that may receive the malleable internal stent 40. In some implementations, the malleable internal stent 40 may be inserted from a proximal opening and advanced toward a distal region so that the distal ancillary extension may occupy a position that may support the distal region against collapse. In certain aspects, the catheter body 20 may be coupled, at a proximal end, to a connector that may be configured for fluid communication with a vacuum source via catheter tubing, and the malleable internal stent 40 may resist radial collapse when the assembly is subjected to a negative pressure differential. In many aspects, where the catheter body 20 defines a chamber having a bottom and a tube in fluid communication with the chamber, the malleable internal stent 40 may be configured to prevent a bottom of the chamber from being drawn into the tube by suction, for instance.

In other aspects, manufacturing and use may include providing the flexible catheter body 20 having a longitudinal bore, providing the malleable internal stent 40, mechanically coupling the functional module 50 such as the biosensor pod 52 to a terminal docking feature of the malleable internal stent 40, inserting the malleable internal stent 40 into the longitudinal bore, and plastically deforming the malleable internal stent 40 after insertion to impart a persistent non-linear configuration to the catheter body 20. In some implementations, the assembly may include affixing a fluid-tight seal at a proximal interface of the catheter body 20 and verifying that the functional module 50 remains seated during bending. Preferably, the catheter body 20 may be supplied with a range of sizes or durometers to accommodate variations in patient anatomy, or the malleable internal stent 40 may be provided in alternative stiffness classes to tailor column strength to expected suction levels, for example.

Figure 2:
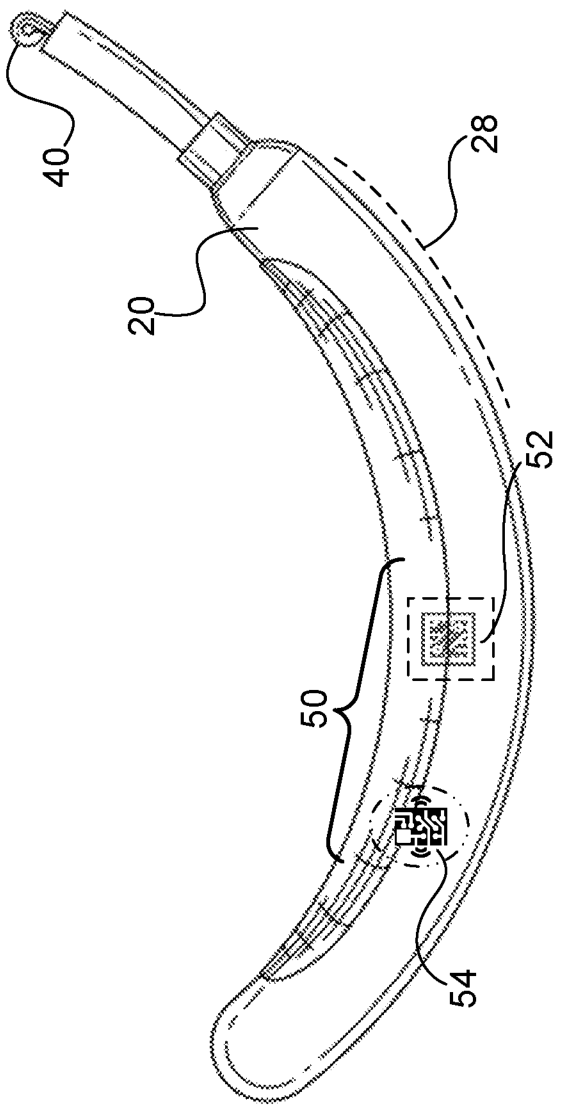
FIG. 2 illustrates a side elevation view of a catheter body, and in particular an arcuate profile of the system.

Referring to FIG. 2, which illustrates a side elevation view of a catheter body 20, the catheter body 20 may present an elongated, flexible form that may be adapted to a female external urinary collection interface and may include catheter tubing integrated within or coupled at a proximal region for fluid communication. In some aspects, the catheter body 20 may define an arcuate profile 28 that may be configured to follow a crescent-like curvature observable in the side view, and the arcuate profile 28 may be selectively reconfigured by an internal support as described below to conform to a specific patient anatomy while maintaining a shaped configuration during use. In various aspects, the catheter body 20 may include a multi-laminate construction having a compliant outer shell and a fluid-wicking inner layer with a textured, fibrous microstructure, and the side view may depict smooth external surfaces terminating in an atraumatic distal region. In certain aspects, an inner concave surface of the catheter body 20 may include a plurality of transverse markings that may be configured to enhance flexibility by distributing bending along short segments that cooperate with internal support to achieve controlled curvature.

In some aspects, a malleable internal stent 40 may be disposed longitudinally within the catheter body 20 such that the malleable internal stent 40 may extend through the catheter body 20 to provide structural support. The malleable internal stent 40 may be semi-rigid and deformable so that a clinician may plastically deform selected portions to modify the arcuate profile 28 without excessive rebound, and the malleable internal stent 40 may possess sufficient column strength to resist radial collapse when the catheter body 20 is subjected to a negative pressure differential via a connector coupled to catheter tubing. In various aspects, the malleable internal stent 40 may be fabricated from a memory metal alloy, a spring-tempered stainless steel, a malleable metal-polymer composite, or a polymeric rod reinforced with fibers to achieve a balance of shape-retention and resilience. In certain implementations, a distal segment of the malleable internal stent 40 may carry an ancillary support structure that may include an extension to reinforce a distal end region of the catheter body 20, which may reduce local inward deflection of a flexible wall under suction and may maintain lumen openness in that region.

In many aspects, the arcuate profile 28 may be established by cooperative interaction between the catheter body 20 and the malleable internal stent 40. The arcuate profile 28 may be adjusted by applying gentle bending moments through the catheter wall while the malleable internal stent 40 is supported against a flat or curved surface, and the adjusted shape may be retained by the material properties of the malleable internal stent 40. Preferably, the arcuate profile 28 may be tuned at one or more bend radii along concave and convex segments to accommodate variability in patient anatomy or positioning and may be restored or further modified as needed during repositioning. In certain aspects, the transverse markings of the catheter body 20 may serve as visual indicators of intended bend zones that may cooperate with the malleable internal stent 40 to distribute strain and to reduce localized kinking, for instance.

In some aspects, at least one functional module 50 may be mechanically coupled to the malleable internal stent 40 at a terminal docking feature such as a coiled end-loop integrally formed with the malleable internal stent 40. The functional module 50 may be configured for reversible installation by a captured loop, friction sleeve, or snap-fit collar so that the functional module 50 may be swapped in clinical settings without specialized tools. In certain implementations, a biosensor pod 52 may be positioned at ends of the malleable internal stent 40 and may include one or more sensors that may monitor a physiological parameter such as pH, temperature, acidity, or presence of blood, and the biosensor pod 52 may be encapsulated in a biocompatible housing that may permit fluid exposure of sensing surfaces while protecting conductors or electronics. In other aspects, a dispenser pod 54 may be used as the functional module 50 and may dispense a substance such as a medication or a dye through a metered or wicking outlet, which may be oriented toward an inner wicking layer of the catheter body 20 or toward an interface region proximate to the distal region.

In various aspects, the catheter body 20 may be configured to connect at a proximal region to a vacuum source by way of catheter tubing so that fluid may be drawn through a defined chamber while the malleable internal stent 40 resists collapse during negative pressure operation. The side elevation of the arcuate profile 28 may indicate that a gentle curvature may align a distal region with an anatomical surface while allowing the proximal region to route tubing without sharp turns. In some implementations, the malleable internal stent 40 may extend substantially along the length of the catheter body 20 so that both distal and proximal regions may benefit from support, and the malleable internal stent 40 may be adjusted after insertion to impart a persistent non-linear configuration suited to a particular patient. Preferably, material selections for the catheter body 20 may include medical-grade silicone for the outer shell and a fibrous or foam-based wicking medium for the inner wicking layer, while the malleable internal stent 40 may be offered in multiple stiffness classes to correspond to ranges of expected suction levels and handling preferences.

Figure 3:
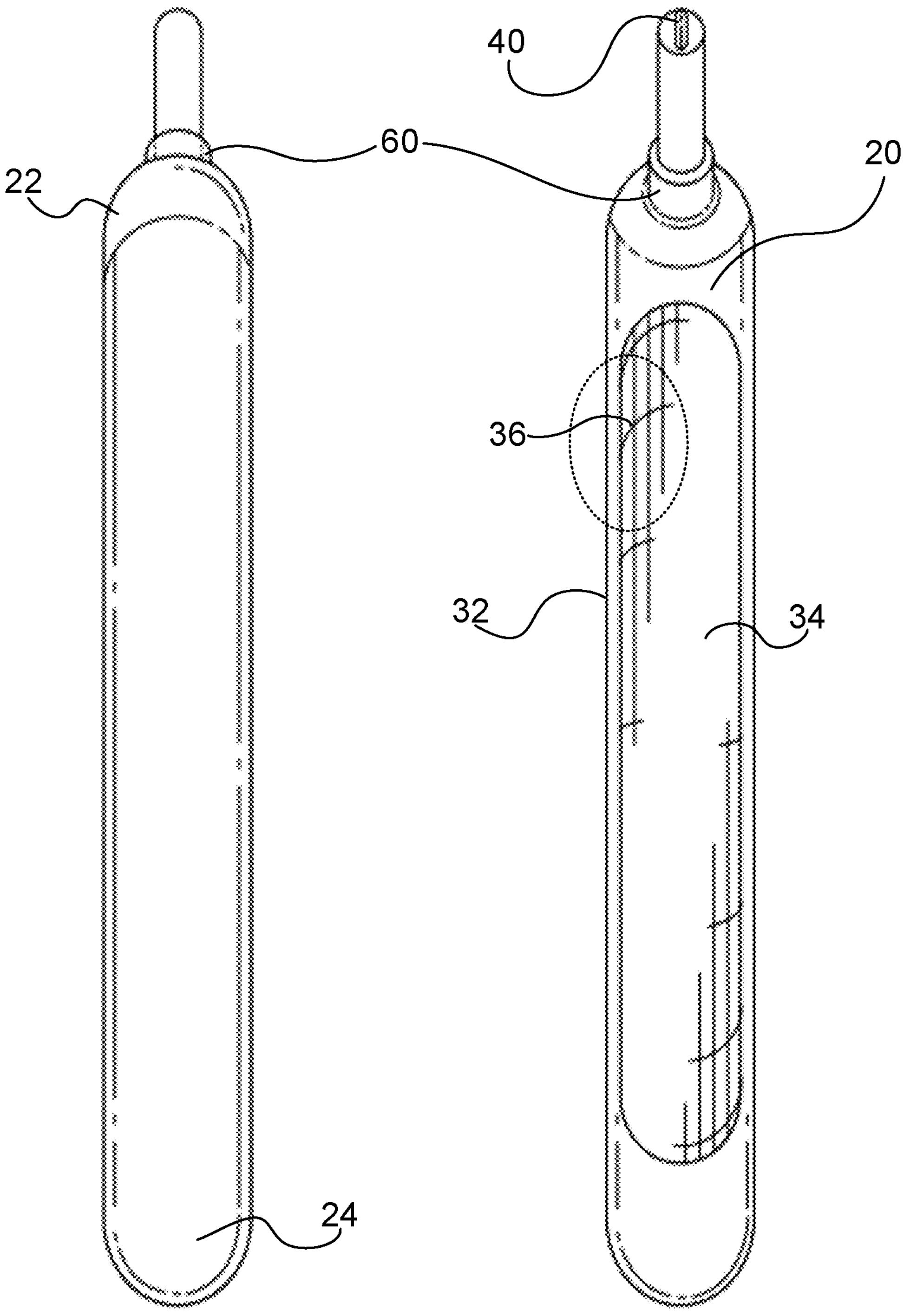
FIG. 3 illustrates a perspective view of a catheter body, the catheter body may include a proximal end and a distal end, and may present an elongated, flexible geometry sized to interface with a female anatomical surface.

Referring to FIG. 3, which illustrates a perspective view of a catheter body 20, the catheter body 20 may include a proximal end 22 and a distal end 24, and may present an elongated, flexible geometry sized to interface with a female anatomical surface. In some aspects, the catheter body 20 may include catheter tubing integrated at the proximal end 22 for routing fluid away from an interface region and toward a downstream collection or vacuum source. In certain aspects, the catheter body 20 may define a longitudinal bore that may be configured to receive a malleable internal stent 40 extending along at least a substantial portion of the length to provide structural support during negative pressure operation. In many aspects, the catheter body 20 may be shaped with a gentle curvature that may be set or adjusted by the malleable internal stent 40 to accommodate anatomical variability and to maintain a shaped configuration during placement and use.

In some aspects, the catheter body 20 may have a multi-laminate construction including a compliant outer shell 32 and a fluid-wicking inner layer 34. The compliant outer shell 32 may include a soft, biocompatible elastomer such as medical-grade silicone, polyurethane, or a thermoplastic elastomer, and may be selected for surface compliance, skin contact properties, and manufacturability, for example. The fluid-wicking inner layer 34 may include a textured, fibrous microstructure configured to transport liquid via capillary action away from the interface region toward the proximal end 22, and may be formed from polyester, rayon, polyolefin nonwoven, foam, or a composite wicking media. In various aspects, the compliant outer shell 32 may be bonded, over-molded, or co-extruded over the fluid-wicking inner layer 34 so that the layers may remain mechanically registered during bending and suction. Preferably, a thickness of the compliant outer shell 32 and a porosity or basis weight of the fluid-wicking inner layer 34 may be tuned to maintain lumen openness and to promote fluid transport without excessive stiffness.

In certain aspects, an inner concave surface of the catheter body 20 may include transverse markings 36 that may be configured to enhance flexibility and to partition bending into shorter segments. The transverse markings 36 may be formed as shallow grooves, ribs, perforation lines, or regions of locally reduced thickness that may cooperate with the malleable internal stent 40 to facilitate controlled reconfiguration of an arcuate profile and to reduce risks of kinking. In some implementations, the transverse markings 36 may serve as visible indicators to guide clinicians where to apply bending forces when customizing shape, and pitch or depth of the transverse markings 36 may vary along the length to produce graded flexibility.

In many aspects, a malleable internal stent 40 may be disposed longitudinally within the catheter body 20 so that the malleable internal stent 40 may extend through the catheter body 20 to provide structural support. The malleable internal stent 40 may be semi-rigid and deformable so that it may be plastically bent to a target curvature while retaining sufficient column strength to resist radial collapse of the catheter body 20 when subjected to a negative pressure differential via the proximal end 22. The malleable internal stent 40 may be fabricated from a memory metal alloy such as nitinol, a malleable stainless steel, an aluminum-bronze wire, or a fiber-reinforced polymeric rod designed for shape-retention and resilience. In some aspects, a distal segment of the malleable internal stent 40 may include or be coupled to an ancillary support structure, which may include an extension configured to reinforce the distal end 24 region so that inward wall deflection may be reduced near the tip during suction operation, for instance. In certain implementations, the malleable internal stent 40 may be supplied in multiple stiffness classes so that clinicians may select a stiffness corresponding to expected suction levels, patient mobility, or desired ease of in situ adjustment.

In some aspects, a connector 60 may be coupled at the proximal end 22 to establish fluid communication with a vacuum source via catheter tubing. The connector 60 may include a barbed, luer, or bayonet interface configured for standard clinical tubing sizes, and may include a gasket, ferrule, or overmold to promote a fluid-tight seal with the proximal end 22. In various aspects, the connector 60 may be arranged so that suction applied through the connector 60 may draw fluid through the fluid-wicking inner layer 34 while the malleable internal stent 40 resists radial collapse of the compliant outer shell 32. Preferably, the geometry near the proximal end 22 may be drafted to minimize abrupt directional changes in flow paths, and an internal diameter of the connector 60 may be selected to reduce pressure drop at representative vacuum levels used in clinical practice.

In other aspects, the distal end 24 may be shaped with a rounded, atraumatic profile that may be soft to the touch due to the compliant outer shell 32, and the fluid-wicking inner layer 34 may extend toward the distal end 24 to draw liquid away from skin surfaces. The transverse markings 36 may continue toward mid-span to cooperate with bending set by the malleable internal stent 40 so that the catheter body 20 may be selectively reconfigured to conform to a specific patient anatomy while maintaining its shaped configuration. In some implementations, the proximal end 22 may further include strain-relief features or overmold transitions that may distribute loads between the connector 60 and the compliant outer shell 32. Preferably, assembly may include inserting the malleable internal stent 40 into the longitudinal bore of the catheter body 20, coupling the connector 60 to the proximal end 22 to achieve a fluid-tight interface, and then plastically deforming the malleable internal stent 40 to impart a persistent, non-linear configuration that aligns the catheter body 20 with an intended anatomical surface, for example.

Figure 4:
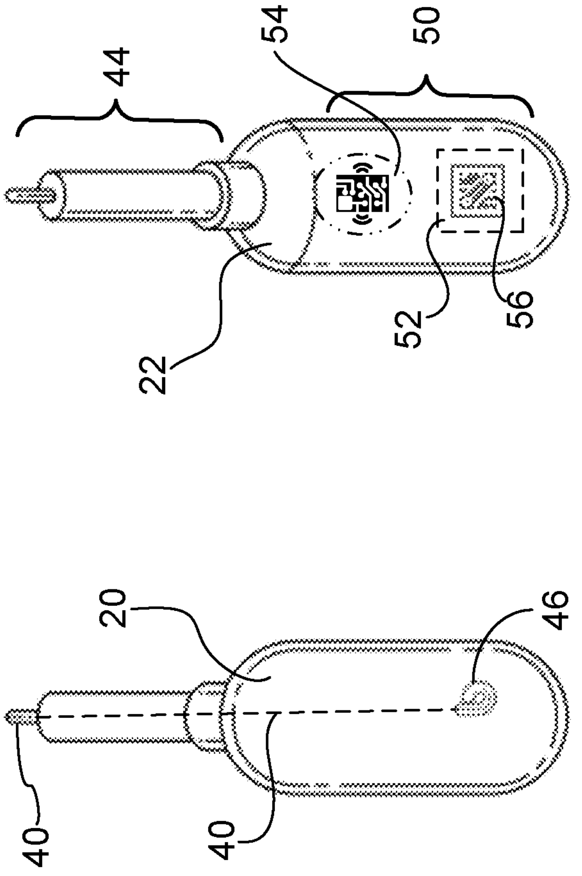
FIG. 4 illustrates a perspective view of a catheter body coupled at a proximal end 22 and equipped with a malleable internal stent and one or more terminal docking features, the catheter body may present an elongated, flexible geometry sized to interface with a female anatomical surface and may include catheter tubing routed from the proximal end to a vacuum source.

Referring to FIG. 4, which illustrates a perspective view of a catheter body 20 coupled at a proximal end 22 and equipped with a malleable internal stent 40 and one or more terminal docking features 44, the catheter body 20 may present an elongated, flexible geometry sized to interface with a female anatomical surface and may include catheter tubing routed from the proximal end 22 to a vacuum source. In some aspects, the malleable internal stent 40 may be disposed longitudinally within the catheter body 20 so that the malleable internal stent 40 may extend through the catheter body 20 to provide structural support during handling and during negative pressure operation. In various aspects, the catheter body 20 may be shaped into a non-linear, arcuate configuration by plastic deformation of the malleable internal stent 40 so that the catheter body 20 may conform to a specific patient anatomy while maintaining its shaped configuration during typical clinical use.

In some aspects, the proximal end 22 may be configured to interface with standard clinical tubing so that suction may be applied to draw liquid from an interface region along an internal flow path. The proximal end 22 may include a strain relief, a compliant overmold, or a tapered geometry that may help reduce stress at the transition between the catheter body 20 and attached tubing. In various implementations, the geometry at the proximal end 22 may be arranged so that flow direction changes may be gradual, which may help reduce local pressure drop during suction. Preferably, the proximal end 22 may be dimensioned for common tube sizes and may include texturing or ridges that may improve grip during installation and removal, for instance.

In many aspects, the malleable internal stent 40 may include at least one terminal docking feature 44 that may be configured to securely receive a functional module 50. The terminal docking feature 44 may be integrally formed or attached to the malleable internal stent 40 and may adopt geometries such as a coiled end-loop 46, a hook, a saddle, or a slotted ferrule so that the functional module 50 may be mechanically coupled without specialized tools. In certain implementations, the coiled end-loop 46 may define a circumference suitable for seating a housing or stem of the functional module 50, and the coiled end-loop 46 may be formed by turning a terminal portion of the malleable internal stent 40 back upon itself to create a resilient, capture-ready loop that may resist dislodgment under bending and vibration.

In some aspects, the functional module 50 may be selected from a biosensor pod 52 or a dispenser pod 54 depending on clinical objectives. The functional module 50 may be removably engaged with the terminal docking feature 44 by a friction fit, snap-fit, twist-lock, or a compressive sleeve that may be compatible with the coiled end-loop 46. In various aspects, the functional module 50 may be positioned near a distal or proximal terminus of the malleable internal stent 40 according to a monitoring or dispensing target region, and multiple functional modules 50 may be used in some configurations if terminal docking features 44 are provided at both ends of the malleable internal stent 40, for example.

In certain aspects, the biosensor pod 52 may include at least one sensor 56 that may be configured to monitor a physiological parameter such as pH, temperature, acidity, or presence of blood. The sensor 56 may be embodied as an electrochemical probe, a thermistor or RTD, an optical absorbance or scattering element, or a colorimetric indicator positioned to contact or view liquid drawn through or across the catheter body 20. In some implementations, the biosensor pod 52 may include an encapsulated electronics package, leads, and a connector header, or a passive indicator that may be read visually. Preferably, the biosensor pod 52 may be packaged in a biocompatible housing that may be smooth, resilient, and shaped to seat within the coiled end-loop 46 while exposing the sensor 56 to a fluid path or a wicking region, for instance.

In other aspects, the dispenser pod 54 may be configured to dispense a substance such as a medication or a dye toward an internal wicking medium or a target surface adjacent to the catheter body 20. The dispenser pod 54 may include a metering orifice, a capillary outlet, or a micro-porous emitter that may control a release rate, and the dispenser pod 54 may be actuated manually or via a controllable valve integrated in the dispenser pod 54. In many implementations, a reversible engagement between the dispenser pod 54 and the terminal docking feature 44 may allow replacement of the dispenser pod 54 when a reservoir is depleted, and the dispenser pod 54 may be oriented so that dispensed material may be carried by suction and wicking toward a collection path without pooling.

In various aspects, the malleable internal stent 40 may be fabricated from a memory metal alloy so that it may be plastically deformed to impart a curvature that persists during use while retaining sufficient column strength to resist radial collapse of the catheter body 20 under a negative pressure differential introduced at the proximal end 22. The malleable internal stent 40 may be offered in multiple stiffness classes to align with different suction levels or patient mobility conditions, and surface finishes of the malleable internal stent 40 near the terminal docking feature 44 may be selected to provide adequate friction for module retention while avoiding abrasion of module housings. Preferably, the cooperative arrangement of the malleable internal stent 40, the terminal docking feature 44, and the coiled end-loop 46 may enable the catheter body 20 to be selectively reconfigured to accommodate patient-specific geometry while providing a standardized mechanical interface for the functional module 50, the biosensor pod 52, or the dispenser pod 54.

Figure 5:
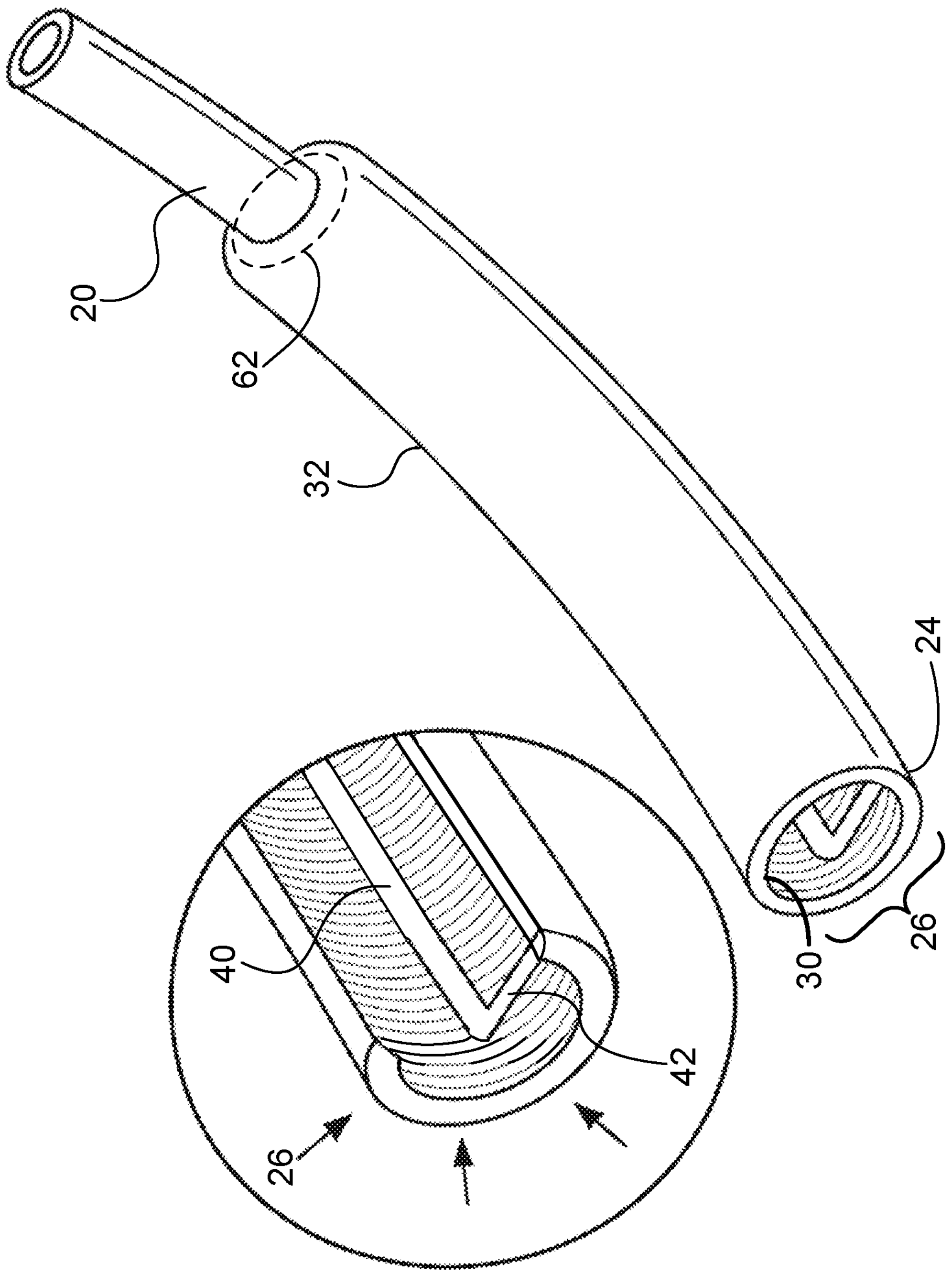
FIG. 5 illustrates an exploded assembly view of a catheter body and a malleable internal stent configured for integration within a longitudinal bore, the catheter body may be elongated and flexible to establish an interface with a patient while routing fluid toward a proximal region.

Referring to FIG. 5, which illustrates an exploded assembly view of a catheter body 20 and a malleable internal stent 40 configured for integration within a longitudinal bore 26, the catheter body 20 may be elongated and flexible to establish an interface with a patient while routing fluid toward a proximal region. In some aspects, the catheter body 20 may include catheter tubing integrated with or joined to a proximal structure so that suction may be applied during operation. In various aspects, the longitudinal bore 26 may extend from a proximal opening toward a distal end 24 to receive the malleable internal stent 40 along a substantial portion of the length, and the malleable internal stent 40 may extend through the catheter body 20 to provide structural support while permitting selective reconfiguration of an arcuate profile that may conform to patient anatomy. In certain implementations, the distal end 24 may be shaped with an atraumatic contour and may cooperate with distal features of the malleable internal stent 40 to resist inward wall movement under negative pressure.

In many aspects, the catheter body 20 may include a multi-laminate construction 30 that may be arranged to balance compliance, comfort, and fluid transport. The multi-laminate construction 30 may include a compliant outer shell 32 and a concentric inner wicking layer (not separately numbered in FIG. 5) that may extend along the longitudinal bore 26 to manage liquid drawn by suction. The compliant outer shell 32 may include medical-grade silicone, thermoplastic elastomer, or polyurethane selected to provide a smooth external surface and a Shore hardness suited to conforming against soft tissue, for example. In some implementations, the inner wicking layer of the multi-laminate construction 30 may include a textured, fibrous microstructure formed from nonwoven polyester, rayon, polyolefin, or foam configured to transport fluid via capillarity toward the proximal region. Preferably, the layers of the multi-laminate construction 30 may be co-extruded, laminated, or overmolded so that bending and local deformation may be distributed without delamination during shape adjustments and suction.

In certain aspects, the malleable internal stent 40 may be semi-rigid and deformable so that a clinician may impart a persistent, non-linear configuration that the catheter body 20 may maintain during use. The malleable internal stent 40 may be fabricated from a memory metal alloy such as nitinol, or from malleable stainless steel, aluminum-bronze, or a fiber-reinforced polymer rod, and dimensions may be selected to provide sufficient column strength to resist radial collapse of the catheter body 20 under representative negative pressure levels. In various implementations, the malleable internal stent 40 may be inserted through the longitudinal bore 26 from the proximal opening so that the malleable internal stent 40 lies generally centered within the catheter body 20 and may be adjusted in situ by hand. In some aspects, surface finishes of the malleable internal stent 40 may be treated to reduce friction against internal layers and to promote smooth advancement during assembly.

In many aspects, the malleable internal stent 40 may include an ancillary support structure 42 located near the distal end 24. The ancillary support structure 42 may include an extension that may project toward a distal interior region to provide localized reinforcement against inward deflection of the compliant outer shell 32 during suction. In certain implementations, the ancillary support structure 42 may be a loop, crossbar, cage, or standoff geometry that may maintain spacing between the compliant outer shell 32 and the inner wicking layer while preserving an open fluid path at the distal end 24. Preferably, the ancillary support structure 42 may be integrally formed with the malleable internal stent 40 or may be mechanically affixed by a crimp, weld, or adhesive-compatible sleeve so that the ancillary support structure 42 remains aligned during bending and repositioning, for instance.

In some aspects, a fluid-tight seal 62 may be positioned at or near the proximal opening of the longitudinal bore 26 after the malleable internal stent 40 is inserted. The fluid-tight seal 62 may include a silicone cork, an elastomeric grommet, a compression ferrule, or an overmolded plug that may prevent ambient air ingress at the proximal interface while permitting catheter tubing or a connector to couple to a suction line. In various implementations, the fluid-tight seal 62 may present a through-passage sized to accept a barbed or luer-style connector, and the fluid-tight seal 62 may be retained by interference fit, adhesive bonding, or overmolding onto the compliant outer shell 32. In certain aspects, the fluid-tight seal 62 may be removable and replaceable to facilitate maintenance or sterilization workflows.

In other aspects, an example assembly method may include providing the catheter body 20 having the longitudinal bore 26, providing the malleable internal stent 40, and inserting the malleable internal stent 40 into the longitudinal bore 26 from the proximal side. The method may include positioning the ancillary support structure 42 proximate to the distal end 24 so that reinforcement may be available where inward collapse may otherwise occur. The method may include affixing the fluid-tight seal 62 at the proximal interface to establish a sealed pathway for suction and plastically deforming the malleable internal stent 40 to impart a persistent curvature that aligns the catheter body 20 with a targeted anatomical surface. Preferably, the multi-laminate construction 30 may be selected with thicknesses and porosities that may cooperate with the stiffness class of the malleable internal stent 40, and the compliant outer shell 32 may be finished with a surface energy compatible with standard medical adhesives or gentle attachment aids when used in clinical settings, for example.

Figure 6:
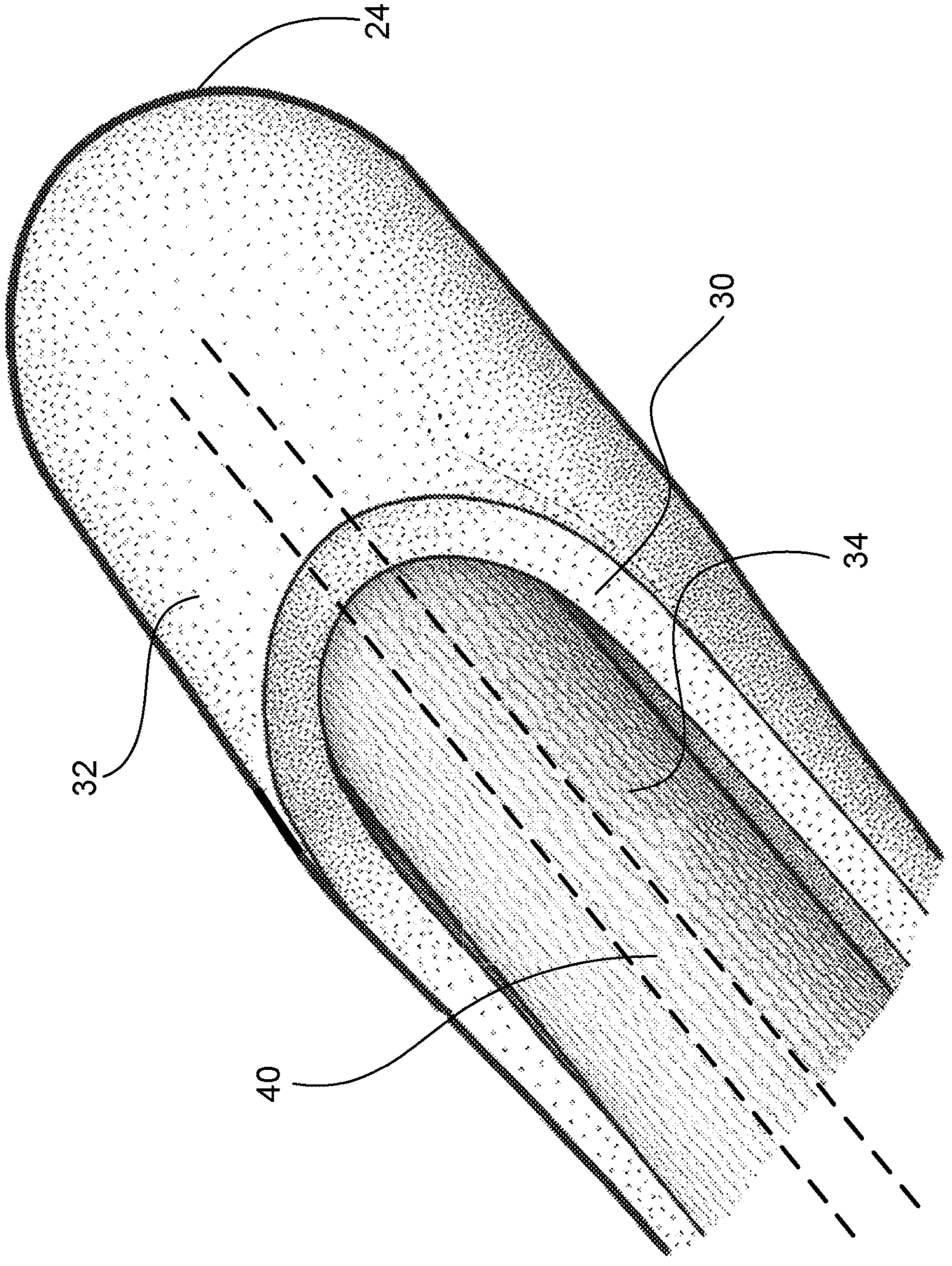
FIG. 6 illustrates a magnified view of a distal end, the distal end may depict a portion of a multi-laminate construction and may show how local structure responds when a negative pressure differential is present along an internal flow path.

Referring to FIG. 6, which illustrates a magnified view of a distal end 24, the distal end 24 may depict a portion of a multi-laminate construction 30 and may show how local structure responds when a negative pressure differential is present along an internal flow path. In some aspects, the multi-laminate construction 30 may include a compliant outer shell 32 and a fluid-wicking inner layer 34 arranged so that liquid may be transported away from skin-contact regions while the compliant outer shell 32 presents a smooth, atraumatic external surface. In various aspects, the view at the distal end 24 may show that when suction is applied from a proximal location, inward deformation of the compliant outer shell 32 may occur if unsupported, and the depiction may indicate how a malleable internal stent 40 may be used to provide structural support to mitigate radial collapse near the distal end 24.

In some aspects, the compliant outer shell 32 may include a soft, biocompatible elastomer selected from medical-grade silicone, thermoplastic elastomer, or polyurethane and may have a thickness profile that may range from about 0.3 mm to about 1.5 mm, but other thicknesses may be used depending on stiffness targets and manufacturing constraints. The compliant outer shell 32 may be formed by extrusion, dip molding, overmolding, or lamination over the fluid-wicking inner layer 34 to promote stable registration during bending. In certain implementations, the compliant outer shell 32 may have a surface finish selected to balance friction and comfort, and a durometer that may fall within a Shore A range between about 10 and about 40 to facilitate conformance to an anatomical surface while maintaining sufficient integrity during suction, for example.

In many aspects, the fluid-wicking inner layer 34 may include a textured, fibrous microstructure that may be visible in the magnified view to illustrate pore distribution and fiber orientation. The fluid-wicking inner layer 34 may include a nonwoven or foam medium engineered for capillary transport, and an average pore size may be tuned within a non-limiting range from about 20 μm to about 500 μm so that liquid may be drawn from the distal end 24 toward a proximal region under both capillary action and applied vacuum. In some implementations, the fluid-wicking inner layer 34 may include rayon, polyester, polyolefin, cellulose-based fibers, or blended structures, and a basis weight and thickness may be adjusted to achieve target wicking rates while allowing bending without kinking. Preferably, the fluid-wicking inner layer 34 may extend to the distal end 24 so that collected liquid may be intercepted near an interface and transported away from skin, for instance.

In certain aspects, the malleable internal stent 40 may be disposed within the multi-laminate construction 30 so that the malleable internal stent 40 extends near the distal end 24 to provide structural support. The malleable internal stent 40 may be semi-rigid and deformable so that a clinician may set a curvature that may persist during use, and the malleable internal stent 40 may possess sufficient column strength to resist radial collapse of the compliant outer shell 32 when a negative pressure differential is present. In various implementations, the malleable internal stent 40 may be fabricated from a memory metal alloy such as nitinol, a malleable stainless steel, or a fiber-reinforced polymeric rod that may be selected to maintain lumen patency near the distal end 24 while allowing incremental shape adjustments. In some aspects, a distal segment of the malleable internal stent 40 may be configured to cooperate with a local internal space so that spacing between the compliant outer shell 32 and the fluid-wicking inner layer 34 is maintained to reduce flow restriction.

In many aspects, the magnified view may emphasize that, under suction, portions of the compliant outer shell 32 may tend to move inward toward the fluid-wicking inner layer 34. The malleable internal stent 40 may counter this motion by acting as an internal support that may limit radial displacement, thereby preserving an open flow corridor adjacent to the fluid-wicking inner layer 34. In some implementations, negative pressure at clinically relevant levels (for example, about 2 kPa to about 30 kPa below ambient) may be applied via a proximal connector and catheter tubing, and the multi-laminate construction 30 together with the malleable internal stent 40 may cooperate to maintain a fluid path continuity from the distal end 24 toward the proximal region. Preferably, the geometry at the distal end 24 may be rounded to distribute contact pressure and to reduce localized stress concentration during bending and suction cycles.

In certain aspects, the multi-laminate construction 30 may be bonded using adhesives compatible with medical device standards, thermal lamination, solvent bonding, or overmolding processes so that shear transfer between the compliant outer shell 32 and the fluid-wicking inner layer 34 may be stable during repeated deformation. The malleable internal stent 40 may be inserted within a longitudinal channel so that the malleable internal stent 40 resides centrally or slightly biased toward an inner concave side of an arcuate profile, which may improve shape-setting ergonomics and local stiffness distribution near the distal end 24. In various implementations, the relative radial placement of the malleable internal stent 40 may be selected to reduce the likelihood of the compliant outer shell 32 contacting the fluid-wicking inner layer 34 under suction-induced loads, thereby limiting occlusion propensity at the distal end 24.

In other aspects, the distal end 24 may include optional contouring or micro-texture features on the compliant outer shell 32 to manage liquid ingress toward the fluid-wicking inner layer 34 without pooling, and radii may be selected to reduce snagging during repositioning. The fluid-wicking inner layer 34 may optionally be treated with hydrophilic finishes or surfactants, and additive packages may be selected to remain stable under expected sterilization methods such as ethylene oxide or gamma irradiation. The malleable internal stent 40 may be provided in multiple stiffness classes so that the balance between shape retention and compliance may be tuned for different patient populations or suction settings. Preferably, the arrangement depicted in FIG. 6 may be implemented so that a practitioner may shape the malleable internal stent 40 to conform the distal end 24 to a patient's anatomy while the multi-laminate construction 30 promotes fluid transport and the compliant outer shell 32 may provide a comfortable interface, for instance.

Figure 7:
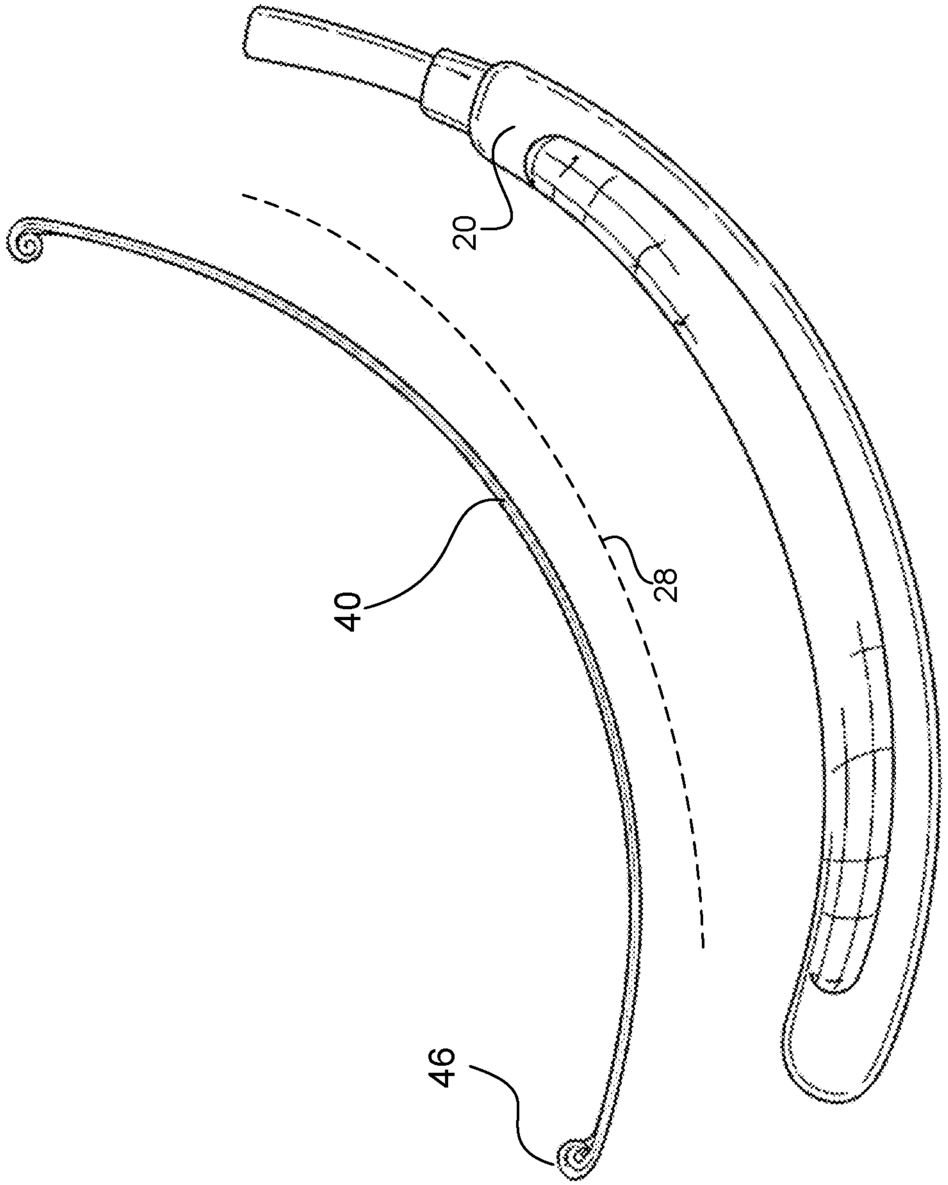
FIG. 7 illustrates an exploded perspective view of a catheter body and a malleable internal stent oriented for assembly, the catheter body may be configured as an elongated, flexible structure that may be shaped to present an arcuate profile for conformance to an anatomical surface.

Referring to FIG. 7, which illustrates an exploded perspective view of a catheter body 20 and a malleable internal stent 40 oriented for assembly, the catheter body 20 may be configured as an elongated, flexible structure that may be shaped to present an arcuate profile 28 for conformance to an anatomical surface. In some aspects, the catheter body 20 may define a hollow interior sized to receive the malleable internal stent 40 so that, after insertion, the malleable internal stent 40 may extend along the length of the catheter body 20 to provide structural support during handling and during negative pressure operation. In various aspects, the arcuate profile 28 may be set by manually bending the malleable internal stent 40 through the wall of the catheter body 20, and the imparted curvature may be maintained during use so the catheter body 20 may retain a configured shape, for instance.

In certain aspects, the catheter body 20 may include a multi-laminate wall construction that may include a compliant outer shell and a fluid-wicking inner layer, and the exploded orientation may be depicted to show how the malleable internal stent 40 may be housed generally centrally within the cross-section. The catheter body 20 may be formed using extrusion, dip molding, overmolding, or lamination, and wall thicknesses may be selected to balance conformance and lumen stability under suction. In some implementations, internal features of the catheter body 20 such as shallow internal channels, sleeves, or guides may be provided to guide the malleable internal stent 40 during insertion and to reduce friction, although such guides may be optional and may not be required for assembly.

In many aspects, the arcuate profile 28 may represent a non-linear curve with one or more bend radii that may be selected to align an interface region of the catheter body 20 with a patient's anatomy while routing a proximal region toward suction tubing without sharp turns. The arcuate profile 28 may be adjusted by applying gentle bending moments at discrete locations, and the final geometry may be fine-tuned in situ after initial placement. Preferably, the arcuate profile 28 may be repeatably adjusted multiple times without material damage to the catheter body 20 due to the cooperation between the flexible wall and the support characteristics of the malleable internal stent 40, for example.

In some aspects, the malleable internal stent 40 may be semi-rigid and plastically deformable so that it may be shaped to a desired curvature and may retain that curvature during clinical use. The malleable internal stent 40 may provide sufficient column strength to resist radial collapse of the catheter body 20 under representative negative pressure differentials applied at a proximal connector. In various implementations, the malleable internal stent 40 may be formed from a memory metal alloy such as nitinol, a malleable stainless steel wire, an aluminum-bronze rod, a fiber-reinforced polymeric rod, or a metal-polymer hybrid selected for combined shape-retentive behavior and resilience. In certain aspects, the malleable internal stent 40 may be sized so that its length extends substantially along the catheter body 20, and its diameter or cross-section may be chosen to provide a target flexural modulus and buckling resistance across anticipated operating conditions.

In many aspects, a coiled end-loop 46 may be integrally formed at a terminal end of the malleable internal stent 40 to serve as a terminal docking feature for optional modules described elsewhere, while in FIG. 7 the coiled end-loop 46 may be visible primarily as a mechanical termination that may simplify handling during assembly. The coiled end-loop 46 may be fabricated by turning a terminal section of the malleable internal stent 40 back upon itself to form a loop of selected circumference and pitch, and the coiled end-loop 46 may provide a capture geometry that may resist axial withdrawal or torsional loosening. In some implementations, the coiled end-loop 46 may contact or seat within an internal feature of the catheter body 20 to limit distal migration of the malleable internal stent 40 during suction cycles.

In certain aspects, assembly may include advancing the malleable internal stent 40 into the catheter body 20 from a proximal opening until the coiled end-loop 46 approaches a distal region inside the catheter body 20. The malleable internal stent 40 may be rotated slightly during insertion to reduce sliding friction, and a small amount of biocompatible lubricant may be used if desired to aid passage along internal liners or sleeves. Once positioned, a clinician may impart the arcuate profile 28 by bending the assembly against a support surface, and the catheter body 20 may retain the configured curvature due to plastic deformation of the malleable internal stent 40. Preferably, any stress concentration at the coiled end-loop 46 may be minimized by smoothing the loop transitions and by selecting a suitable loop diameter to distribute local bending strain, for instance.

In other aspects, the exploded perspective may illustrate that the catheter body 20 and the malleable internal stent 40 are separable subassemblies that may be supplied in different sizes or stiffness classes. The catheter body 20 may be offered in a range of lengths and wall constructions to address different patient anatomies and suction scenarios, and the malleable internal stent 40 may be offered in multiple stiffness grades so users may select a configuration that may provide a desired balance of conformity and lumen support. In various implementations, manufacturing quality controls such as bend-retention testing and simulated suction collapse testing may be applied to the malleable internal stent 40 and the catheter body 20 to verify that the assembled configuration may resist radial collapse while permitting repeatable reconfiguration of the arcuate profile 28.

Figure 8:
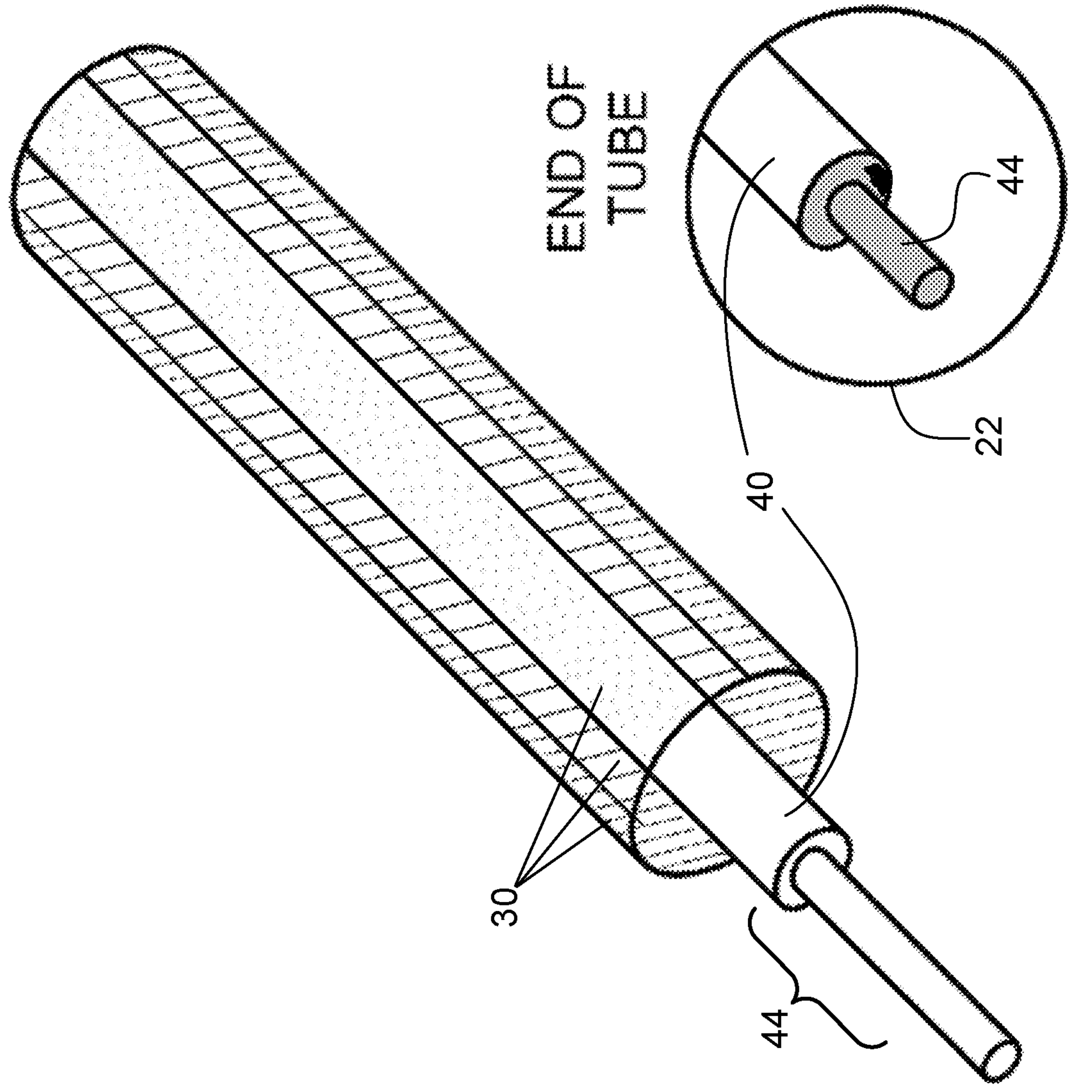
FIG. 8 illustrates a longitudinal, partially bisected view centered about a proximal end, the proximal end may be shown in fluid communication with catheter tubing via an internal passage while a multi-laminate construction is visible in section.
Figure 9:
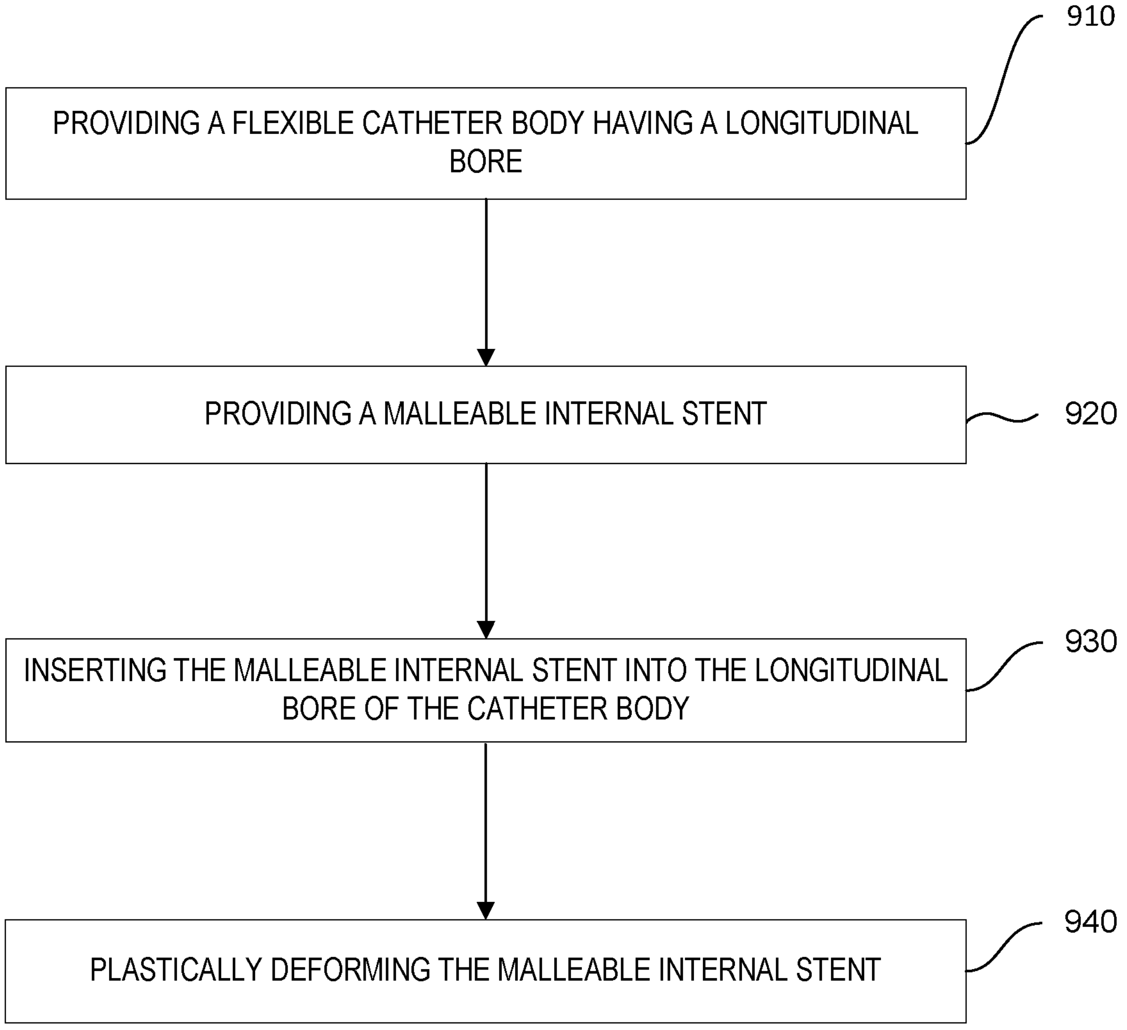
FIG. 9 is a flow chart illustrating the process of deforming the malleable internal stent by way of inserting the malleable internal stent into the longitudinal bore of the catheter body.

Referring to FIG. 8, which illustrates a longitudinal, partially bisected view centered about a proximal end 22, the proximal end 22 may be shown in fluid communication with catheter tubing via an internal passage while a multi-laminate construction 30 is visible in section. In some aspects, the multi-laminate construction 30 may include a compliant external wall and a concentric fluid-wicking medium arranged so that liquid may be transported away from a patient interface toward the proximal end 22 under capillary action and suction. In various aspects, a malleable internal stent 40 may be disposed longitudinally within the multi-laminate construction 30, and the malleable internal stent 40 may extend through the catheter to provide structural support and a shape-retentive framework that may be selectively configured to conform the catheter body to a specific patient anatomy. In certain implementations, the cross-section may depict the malleable internal stent 40 centrally or slightly offset toward an inner concave region so that bending moments may be more predictably introduced when shaping the assembly, for instance.

In some aspects, the proximal end 22 may be configured to couple to a vacuum source through a connector and tubing so that a negative pressure differential may be applied to the interior flow path. The proximal end 22 may include a seat or recess into which a fluid-tight element, such as a cork or grommet, may be installed to reduce air ingress and to stabilize the interface under suction. In various implementations, the internal flow path near the proximal end 22 may be drafted with gradual transitions so that pressure drop may be moderated, and the malleable internal stent 40 may be terminated proximally at a position that may avoid obstructing flow while still supporting the adjacent wall. Preferably, the geometry adjacent to the proximal end 22 may be dimensioned to mate with standard clinical tubing sizes using barbed, luer, or similar interfaces, for example.

In many aspects, the multi-laminate construction 30 may be defined by a compliant outer shell and a fluid-wicking inner layer that may be joined by lamination, overmolding, co-extrusion, or adhesive bonding. The compliant outer shell of the multi-laminate construction 30 may include medical-grade silicone, polyurethane, or thermoplastic elastomer selected to present a smooth, atraumatic surface while accommodating repeated bending, and a wall thickness may be selected to balance conformance and resistance to buckling under vacuum. The fluid-wicking inner layer of the multi-laminate construction 30 may include a textured, fibrous microstructure formed from nonwoven polyester, rayon, polyolefin, cellulose, foam, or composite wicking materials that may transport fluid by capillarity, with an average pore size selected to maintain flow continuity toward the proximal end 22 under expected suction levels. In certain implementations, the multi-laminate construction 30 may define a chamber region upstream of an internal tube, and the arrangement of materials may be selected so that a bottom surface of such a chamber may remain spaced from an inlet opening during suction.

In certain aspects, the malleable internal stent 40 may be semi-rigid and plastically deformable so that a caregiver may shape the catheter into a persistent, non-linear configuration. The malleable internal stent 40 may be fabricated from a memory metal alloy such as nitinol, a malleable stainless steel, a bronze alloy, a fiber-reinforced polymeric rod, or a metal-polymer hybrid sized to provide sufficient column strength to resist radial collapse when the proximal end 22 is subjected to negative pressure. In some implementations, a distal portion of the malleable internal stent 40 (not depicted at this proximal-focused section) may include an ancillary support extension that may reinforce a distal region to reduce inward wall movement and preserve patency. In many aspects, the malleable internal stent 40 may be surface-finished to reduce friction against inner laminate surfaces and may be inserted through a longitudinal bore during assembly, after which in situ shaping may be performed to finalize patient-specific curvature.

In various aspects, a terminal docking feature 44 may be provided on the malleable internal stent 40 to mechanically receive at least one functional module in embodiments that include monitoring or dispensing. The terminal docking feature 44 may include a coiled end-loop formed integrally with the malleable internal stent 40, a crimped ferrule with a slot, a hook, or a saddle that may receive a pod stem or sleeve with frictional or snap engagement. In some implementations, when the terminal docking feature 44 is positioned proximally to the section shown, the geometry may be oriented so that any seated module may be exposed to the internal flow path while remaining clear of the primary lumen to avoid significant pressure losses. Preferably, dimensions of the terminal docking feature 44 may be selected to resist axial migration during vibration and bending while allowing reversible installation of a functional module, for instance.

While a particular form of the invention has been illustrated and described, it will be apparent that various modifications can be made without departing from the spirit and scope of the invention. For example, the terminal docking feature that receives a functional module may be implemented as a slotted ferrule or snap-fit saddle instead of a coiled end-loop, and the distal ancillary support may employ a cage or crossbar configuration to tune anti-collapse stiffness while retaining the same layered catheter body and proximal connector interfaces. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A formable female external catheter system, the system comprising:

an elongated, flexible catheter body comprising catheter tubing; and a semi-rigid, malleable internal stent disposed longitudinally within the catheter body, the internal stent being deformable and possessing sufficient column strength to resist radial collapse of the catheter body, wherein the internal stent extends through the catheter body to provide structural support and wherein the deformability allows the catheter body to be selectively reconfigured to conform to a specific patient anatomy while maintaining the catheter body's shaped configuration, wherein at least one functional module is mechanically coupled to the internal stent, wherein the internal stent comprises at least one terminal docking feature configured to securely receive the at least one functional module, and wherein the at least one terminal docking feature comprises a coiled end-loop integrally formed with the internal stent.

2. The system of claim 1, wherein the at least one functional module is a biosensor pod positioned at ends of the malleable internal stent.

3. The system of claim 2, wherein the biosensor pod comprises a sensor configured to monitor a physiological parameter selected from the group consisting of pH, temperature, acidity, and a presence of blood.

4. The system of claim 1, wherein the at least one functional module is a dispenser pod configured to dispense a substance.

5. The system of claim 4, wherein the substance is selected from the group consisting of a medication and a dye.

6. The system of claim 1, wherein a distal end of the internal stent comprises an ancillary support structure comprising an extension configured to provide structural reinforcement to a distal end of the catheter body.

7. The system of claim 1, wherein the internal stent is fabricated from a memory metal alloy.

8. The system of claim 1, wherein an inner concave surface of the catheter body comprises a plurality of transverse markings configured to enhance flexibility, and wherein the internal stent is deformed to reconfigure an arcuate profile of the catheter body.

9. The system of claim 1, wherein the catheter body has a multi-laminate construction comprising a compliant outer shell and a fluid-wicking inner layer, and wherein the fluid-wicking inner layer comprises a material having a textured, fibrous microstructure.

10. The system of claim 1, wherein the functional module comprises a biosensor pod configured to communicate data wirelessly.

11. The system of claim 1, wherein the functional module is removably engaged with the terminal docking feature.

12. The system of claim 1, wherein the functional module is interchangeable.

13. A formable female external catheter system, the system comprising:

an elongated, flexible catheter body comprising catheter tubing; and a semi-rigid, malleable internal stent disposed longitudinally within the catheter body, the internal stent being deformable and possessing sufficient column strength to resist radial collapse of the catheter body, wherein the internal stent extends through the catheter body to provide structural support and wherein the deformability allows the catheter body to be selectively reconfigured to conform to a specific patient anatomy while maintaining the catheter body's shaped configuration, wherein a proximal end of the catheter body is coupled to a connector configured for fluid communication with a vacuum source, and wherein the radial collapse is resisted when the system is subjected to a negative pressure differential via the connector, wherein the catheter body defines a chamber having a bottom, and a tube in fluid communication with the chamber, and wherein the internal stent is configured for preventing a bottom of the chamber from being sucked into the tube.

14. The system of claim 13, wherein at least one functional module is mechanically coupled to the internal stent.

15. The system of claim 14, wherein the functional module comprises a biosensor pod configured to monitor a physiological parameter selected from the group consisting of pH, temperature, acidity, and a presence of blood.

16. The system of claim 14, wherein the functional module is removably engaged with a terminal docking feature of the internal stent.

17. The system of claim 13, wherein the internal stent is fabricated from a memory metal alloy.

18. The system of claim 13, wherein the catheter body has a multi-laminate construction comprising a compliant outer shell and a fluid-wicking inner layer.

* * * * *